US011118161B2

(12) United States Patent
Kim et al.

(10) Patent No.: US 11,118,161 B2
(45) Date of Patent: Sep. 14, 2021

(54) METHOD FOR DIRECT TRANSDIFFERENTIATION REPROGRAMMING INTO NEURONS USING ELECTROMAGNETIC-INDUCED METAL NANOPARTICLES

(71) Applicant: DONGGUK UNIVERSITY INDUSTRY-ACADEMY COOPERATION FOUNDATION, Seoul (KR)

(72) Inventors: Jongpil Kim, Seoul (KR); Junsang Yoo, Seoul (KR)

(73) Assignee: DONGGUK UNIVERSITY INDUSTRY-ACADEMY COOPERATION FOUNDATION

( * ) Notice: Subject to any disclaimer, the term of this patent is extended or adjusted under 35 U.S.C. 154(b) by 24 days.

(21) Appl. No.: 15/770,550

(22) PCT Filed: Sep. 21, 2016

(86) PCT No.: PCT/KR2016/010537
§ 371 (c)(1),
(2) Date: Apr. 24, 2018

(87) PCT Pub. No.: WO2017/073910
PCT Pub. Date: May 4, 2017

(65) Prior Publication Data
US 2019/0062702 A1  Feb. 28, 2019

(30) Foreign Application Priority Data

Oct. 26, 2015  (KR) .................. 10-2015-0148790
Nov. 17, 2015  (KR) .................. 10-2015-0161299

(51) Int. Cl.
*C12N 5/0793*  (2010.01)
*A61K 35/30*  (2015.01)
(Continued)

(52) U.S. Cl.
CPC ............ *C12N 5/0619* (2013.01); *A61K 35/30* (2013.01); *A61P 25/00* (2018.01);
(Continued)

(58) Field of Classification Search
CPC .. C12N 5/0619; C12N 13/00; C12N 2529/00; C12N 2506/1307; A61P 25/00; A61K 35/30
See application file for complete search history.

(56) References Cited

FOREIGN PATENT DOCUMENTS

KR  10-2011-0134252 A  12/2011
KR  10-2015-0015294 A  2/2015
(Continued)

OTHER PUBLICATIONS

Brewer et al. Isolation and culture of adult neurons and neurospheres. Nature Protocols (2007), 2(6), 1490-1498. (Year: 2007).*
(Continued)

*Primary Examiner* — Sean C. Barron
(74) *Attorney, Agent, or Firm* — Riverside Law LLP

(57) ABSTRACT

The present invention relates to a method for direct transdifferentiation into neurons using metal nanoparticles magnetized by an electromagnetic field, and to a cell therapeutic agent for the treatment of cerebral nerve diseases, comprising neurons differentiated by the method. In the present invention, it was specifically verified that the direct transdifferentiation efficiency into neurons can be remarkably improved through the above method and the symptoms of cerebral nerve diseases, such as a stroke, can be effectively alleviated. Therefore, in the treatment of degenerative cerebral nerve diseases, the target therapy is expected to be implemented through a more fundamental approach.

5 Claims, 19 Drawing Sheets

(51) Int. Cl.
*C07K 14/47* (2006.01)
*C12N 13/00* (2006.01)
*A61P 25/00* (2006.01)

(52) U.S. Cl.
CPC .......... *C07K 14/4702* (2013.01); *C12N 13/00* (2013.01); *C12N 2501/60* (2013.01); *C12N 2506/1307* (2013.01); *C12N 2510/00* (2013.01); *C12N 2529/00* (2013.01)

(56) References Cited

FOREIGN PATENT DOCUMENTS

| WO | WO-2014125256 | A1 | * | 8/2014 | ......... A61K 38/1709 |
| WO | WO-2014168585 | A1 | * | 10/2014 | ........... C12N 5/0075 |
| WO | WO-2014188420 | A1 | * | 11/2014 | ........... C12N 5/0068 |
| WO | WO-2015057015 | A1 | * | 4/2015 | |

OTHER PUBLICATIONS

Lide et al. (CRC Handbook of Chemistry and Physics (Internet version 2005) <http://www.hbcpentbase.com> (Year: 2005).*
Pfisterer, et al., "Direct conversion of human fibroblasts to dopaminergic neurons," PNAS, 2011, 108 (25):10343-10348.
Choi et al., "Stimulation of neural differentiation in human bone marrow mesenchymal stem cells by extremely low-frequency electromagnetic fields incorporated with mnps," Applied Biochemistry and Biotechnology, 2014, 4:1233-1245.
Glaser, et al., "Neuronal adhesion, proliferation and differentiation of embryonic stem cells on hybrid scaffolds made of xanthan and magnetite nanoparticles," Biomedical Materials, 2015, vol. 10(4), Article No. 045002.
Lee et al., "The generation of iPS cells using non-viral magnetic nanoparticlebased transfection," Biomaterials, 2011, 32(28):6683-6691.

* cited by examiner

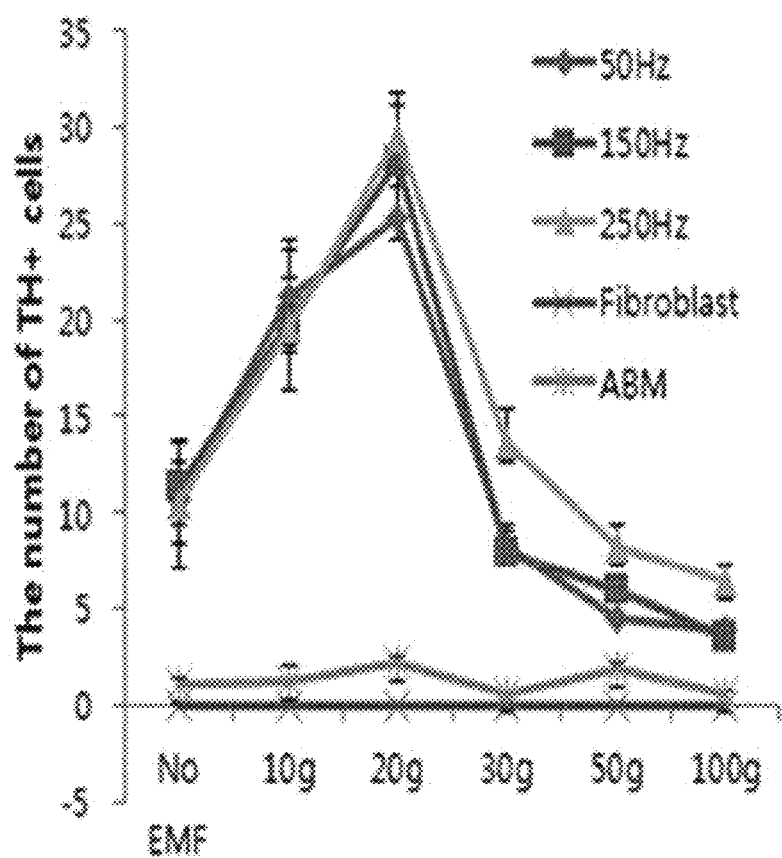

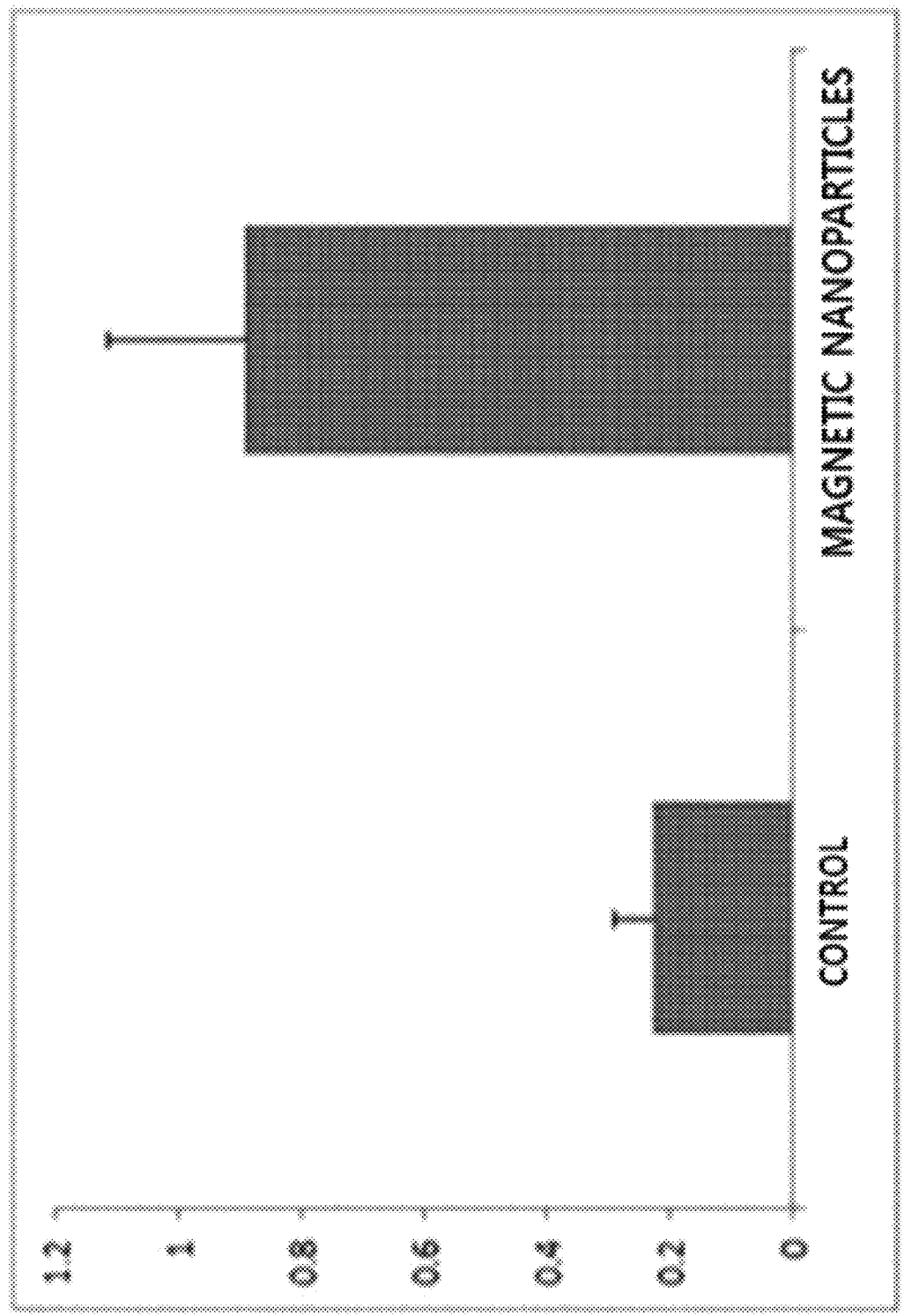

METHOD FOR DIRECT TRANSDIFFERENTIATION REPROGRAMMING INTO NEURONS USING ELECTROMAGNETIC-INDUCED METAL NANOPARTICLES

CROSS-REFERENCE TO RELATED APPLICATIONS

This application is the U.S. national phase application filed under 35 U.S.C. § 371 claiming benefit to PCT International Application No. PCT/KR2016/010537, filed on Sep. 21, 2016, which claims priority to Korean Patent Application Serial No. 10-2015-0148790, filed on Oct. 26, 2015 and Korean Patent Application Serial No. 10-2015-0161299, filed on Nov. 17, 2015, the disclosure of which is incorporated herein by reference in its entirety.

TECHNICAL FIELD

The present invention relates to a method for direct transdifferentiation reprogramming into various neurons using electromagnetic-induced metal nanoparticles, and to a cell therapeutic agent for the treatment of cerebral nerve diseases, comprising various neurons differentiated by the method.

BACKGROUND ART

In the treatment of cerebral nerve diseases, such as Alzheimer's disease, Parkinson's disease, a cerebral infarction, a cerebral hemorrhage, and a spinal cord injury/disease, new therapeutic candidate materials through regeneration of neurons have variously appeared, and as a solution to the treatment, various methods of treating cerebral nerve diseases by creating a patient-specific therapeutic cell using an embryonic stem cell, a pluripotent stem cell, and the like and administering the therapeutic cell have emerged. However, when these undifferentiated pluripotent stem cells are transplanted, there is a limitation in utilizing the pluripotent stem cells as a therapeutic agent because there is a risk that the pluripotent stem cells cause cancer.

As one of the methods for solving the aforementioned problem, a direct transdifferentiation reprogramming technology of inducing direct conversion into a desired cell without going through a pluripotent stem cell step has drawn attention. When this technology is applied, this technology is expected to be effectively used for the treatment of cerebral nerve diseases by directly changing the fate of the cell to manufacture nerve cells in vivo and in vitro, but the technology also does not have a high direct transdifferentiation efficiency into neurons, so that it is also unreasonable to substantially apply the technology to a clinical setting. Thus, attempts to increase the direct transdifferentiation efficiency into neurons have been made (Korean Patent Application Laid-Open No. 10-2015-0015294), but a technology capable of inducing direct transdifferentiation reprogramming, which can be efficiently used even in vivo for actual cell therapy, is still insufficient.

DISCLOSURE

Technical Problem

The present invention has been conceived to solve the aforementioned problems, and the present inventors verified that by using electromagnetic-induced metal nanoparticles by an electromagnetic field, a direct transdifferentiation reprogramming efficiency into neurons in vivo and in vitro can be remarkably enhanced and there are natural differentiation into neurons and a specific neuron protective effect through the natural differentiation, thereby completing the present invention based on this.

Thus, an object of the present invention is to provide a method for direct transdifferentiation of adult cells into neurons, the method comprising applying an electromagnetic field to metal nanoparticles brought into contact with adult cells into which a transcription factor is introduced.

Further, another object of the present invention is to provide a method for natural differentiation into neurons, the method comprising applying an electromagnetic field to metal nanoparticles brought into contact with neural stem cells or neural precursor cells.

In addition, still another object of the present invention is to provide a pharmaceutical composition for the treatment of cerebral nerve diseases, comprising neurons differentiated by the method.

Furthermore, yet another object of the present invention is to provide a cell therapeutic agent for the treatment of cerebral nerve diseases, comprising neurons differentiated by the method.

However, technical problems to be achieved by the present invention are not limited to the aforementioned problem, and other problems that are not mentioned may be clearly understood by a person skilled in the art from the following description.

Technical Solution

In order to achieve the above-described objects of the present invention, the present invention provides a method for direct transdifferentiation of adult cells into neurons, the method comprising applying an electromagnetic field to metal nanoparticles brought into contact with adult cells into which a transcription factor is introduced.

As an exemplary embodiment of the present invention, the transcription factor may be one or more selected from the group consisting of Ascl1, Nurr1, Pitx3, and Lmx1.

As an exemplary embodiment of the present invention, the metal nanoparticles may be one selected from the group consisting of gold nanoparticles, silver nanoparticles, and magnetic nanoparticles.

As another exemplary embodiment of the present invention, the adult cells may be all somatic cells except for fibroblasts and other neurons.

As still another exemplary embodiment of the present invention, the electromagnetic field may be applied at an intensity of 5 Gauss to 100 Gauss.

As yet another exemplary embodiment of the present invention, the electromagnetic field may be applied at a frequency of 10 Hz to 500 Hz.

As yet another exemplary embodiment of the present invention, the neurons differentiated by the method may be all types of neurons, such as dopaminergic neurons, GABAergic neurons, and glutamate neurons.

Further, the present invention provides a method for natural differentiation into neurons, the method comprising applying an electromagnetic field to metal nanoparticles brought into contact with neural stem cells or neural precursor cells.

In addition, the present invention provides a pharmaceutical composition for the treatment of cerebral nerve diseases, comprising neurons differentiated by the method.

Furthermore, the present invention provides a cell therapeutic agent for the treatment of cerebral nerve diseases, comprising neurons differentiated by the method.

As an exemplary embodiment of the present invention, the cerebral nerve disease may be one selected from the group consisting of Alzheimer's disease, Parkinson's disease, cerebral infarctions, cerebral hemorrhages, and strokes.

Further, the present invention provides a method for treating a cerebral nerve disease, the method comprising administering the cell therapeutic agent to an individual.

Furthermore, the present invention provides a use of preparing a therapeutic agent for the treatment of cerebral nerve diseases of neurons differentiated by the method.

Advantageous Effects

A method for direct transdifferentiation reprogramming into neurons according to the present invention induces reprogramming into neurons using electromagnetic-induced metal nanoparticles, and in the present invention, it was specifically verified that the direct transdifferentiation reprogramming efficiency into neurons in vivo and in vitro can be remarkably improved through the above method and when this technology is applied to the brain in vivo, symptoms of cerebral nerve diseases, such as Alzheimer's disease, Parkinson's disease, cerebral infarctions, and cerebral hemorrhages, can be effectively alleviated through neuranagenesis. Therefore, the method is expected to be usefully used as a technology for the treatment of cerebral nerve diseases.

Further, a cell therapeutic technology for the treatment of various cerebral nerve diseases utilizing differentiated neurons was established, and this technology non-invasively induces direct transdifferentiation reprogramming using a physical electromagnetic field, and thus can lead to an efficient neural treatment while being safe and having fewer side effects. Furthermore, even when the neural treatment is completed, there is an advantage in that the nerve regeneration effect can be adjusted depending on the therapeutic degree by simply removing an electromagnetic field treatment.

DESCRIPTION OF DRAWINGS

FIG. 3 is a result comparing changes in the number of TH+ neurons according to the changes in intensity (10 G, 20 G, 30 G, 50 G, and 100 G) and frequency (50 Hz, 150 Hz, and 250 Hz) of an electromagnetic field.

FIG. 4b is a result verifying a change of AADC through RT-PCR when electromagnetic-induced magnetic nanoparticles are used.

MODES OF THE INVENTION

Figure 1:
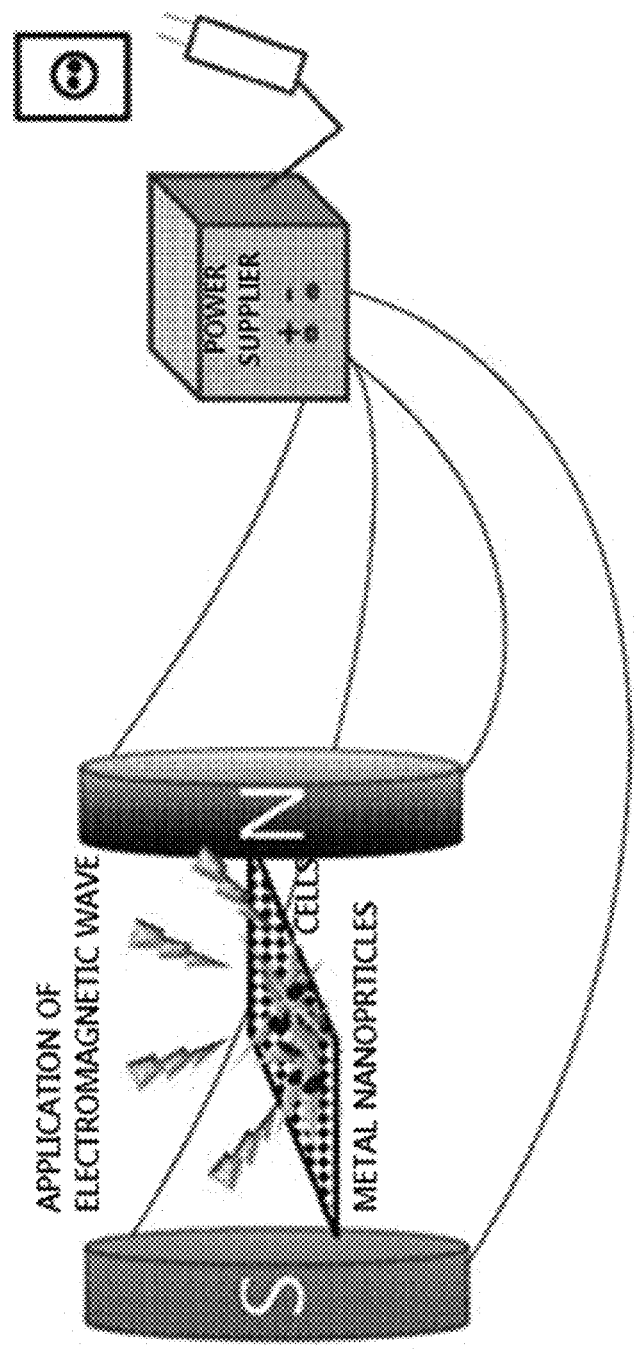
FIG. 1 is a view schematically illustrating a method for direct transdifferentiation reprogramming into neurons by utilizing electromagnetic-induced metal nanoparticles (gold nanoparticles, silver nanoparticles, and magnetic nanoparticles) of the present invention.

The present inventors verified that a direct transdifferentiation reprogramming efficiency into various neurons can be remarkably enhanced using electromagnetic-induced metal nanoparticles, and the direct transdifferentiation efficiency can be freely adjusted by adjusting the applied electromagnetic field during this process. Further, by applying this method in vivo, the present inventors specifically verified that there are effects of remarkably enhancing a direct transdifferentiation efficiency into neurons and alleviating symptoms, even in an experiment using a degenerative cerebral nerve disease animal model, thereby completing the present invention based on this.

Hereinafter, the present invention will be described in detail.

The present invention provides a method for direct transdifferentiation of adult cells into neurons, the method comprising applying an electromagnetic field to metal nanoparticles brought into contact with adult cells into which a transcription factor is introduced, and provides a method for natural differentiation into neurons, the method comprising applying an electromagnetic field to metal nanoparticles brought into contact with neural stem cells or neural precursor cells.

The term "adult cells" as used herein refers to cells in a state where multipotency referring to an ability to be differentiated into various types of cells is completely or mostly lost, as cells in which differentiation occurred, and may be fibroblasts and all somatic cells except for other neurons.

The term "neural stem cells" as used herein refers to multipotent stem cells capable of being differentiated into nerve cells such as neurons, astrocytes, and oligodendrocytes, and may be embryonic stem cells or dedifferentiated stem cells, but the neural stem cells are not limited thereto.

A pre-treatment process of adult cells as used herein refers to the introduction of a neural-inducing transcription factor and the treatment with a neural-inducing substance, which are conventionally known. Further, the introduction of a transcription factor may be carried out through a method well known in the art, such as a method using viruses, and preferably, one or more selected from the group consisting of Ascl1, Nurr1, Pitx3, and Lmx1 may be introduced, but any transcription factor may be included without limitation as long as it is a transcription factor for direct transdifferentiation into neurons.

The term "neurons" as used herein refers to dopaminergic neurons, GABAergic neurons, glutamate neurons, spinal cord neurons, and all types of neurons, and these neurons are positioned in the brain and the spine to constitute the central nervous system. These neurons serve to adjust all types of cerebral functions, such as memory, thinking, postural reflex, movement, and reward-related behavior, and play an important role in the treatment of cerebral nerve diseases.

The term "direct transdifferentiation" as used herein refers to a technology of inducing conversion between adult cells having completely different cell types, and is different from the technology in the related art, in that the this technology induces direct conversion into a desired cell without going through a step of preparing induced pluripotent stem cells. Currently, the availability of the direct transdifferentiation technology has been recognized in disease modeling, discovery of a new medicine, gene therapy, regenerative medicine, and the like, studies on the treatment of cerebral nerve diseases using the same have been actively conducted, but it is difficult to apply the technology to a practical clinical setting due to a low differentiation efficiency of the technology. Further, even though the application of in vivo transdifferentiation through the direct transdifferentiation reprogramming has a clinically significant meaning, there is a problem in commercialization due to the absence of an appropriate induction method. Thus, the present invention is intended to enhance the direct transdifferentiation of adult cells into neurons and the natural differentiation efficiency into neurons, in vivo and in vitro, by using electromagnetic-induced metal nanoparticles.

More specifically, in order to enhance the direct transdifferentiation efficiency into neurons, after adult cells into which a transcription factor was introduced were positioned on metal nanoparticles, electromagnetism was induced in the metal nanoparticles by applying an electromagnetic field, and after metal nanoparticles and a related transcription factor were both injected into the brain which is in the body of an animal, an electromagnetic field was directly applied to the animal.

In the present invention, the electromagnetic-induced metal nanoparticles promote direct transdifferentiation of adult cells into neurons, and may preferably gold, silver, or magnetic nanoparticles, but the metal nanoparticles are not limited thereto.

Further, the electromagnetic field may be applied preferably at an intensity of 5 Gauss to 50 Gauss and/or a frequency of 10 Hz to 500 Hz, but the intensity and the frequency are not limited thereto.

An exemplary embodiment of the present invention may enhance the direct transdifferentiation efficiency into neurons by adjusting the intensity and wavelength of an electromagnetic field to be applied to metal nanoparticles, and it was verified that when not only gold nanoparticles, but also silver or magnetic nanoparticles are used, an excellent effect could be obtained (see Examples 1 and 2). In addition, it was verified that even in an in vivo experiment using an animal model, the direct transdifferentiation efficiency into neurons was enhanced likewise as described above, and cerebral nerve disease-related symptoms were clearly alleviated (see Examples 3 and 4), and through the method of the present invention, it was experimentally verified that the natural differentiation efficiency into neurons was also enhanced, and the neurons could be usefully used for the treatment of cerebral nerve diseases (see Examples 5 and 6).

Thus, the present invention provides a cell therapeutic agent for the treatment of cerebral nerve diseases, comprising neurons differentiated by the method.

The term "treatment" as used herein refers to all actions in which symptoms of the cerebral nerve disease are ameliorated or beneficially altered by administering the cell therapeutic agent according to the present invention.

The "cerebral nerve disease" which is a disease to be treated by the present invention collectively refers to various diseases associated with particularly, cerebral nerves, and may be preferably Alzheimer's disease, Parkinson's disease, a cerebral infarction, a cerebral hemorrhage or stroke, and a spinal cord injury/disease, but the cerebral nerve disease is not limited thereto.

In the present invention, "a cell therapeutic agent" refers to a drug used for the purpose of treatment, diagnosis, and prevention, by using a cell or tissue prepared through isolation from a human, culture and specific operation, and specifically, it refers to a drug used for the purpose of treatment, diagnosis, and prevention through a series of actions of in vitro multiplying and sorting living autologous, allogenic and xenogenic cells or changing the biological characteristics of cells by other methods for the purpose of recovering the functions of cells and tissues.

Meanwhile, another aspect of the present invention provides a method for treating a cerebral nerve disease, the method comprising administering the cell therapeutic agent to an individual.

In the present invention, "an individual" refers to a subject in need of treatment of a disease, and more specifically, refers to a mammal such as a human or a non-human primate, a mouse, a rat, a dog, a cat, a horse, and a cow.

Hereinafter, preferred Examples for helping the understanding of the present invention will be suggested. However, the following Examples are provided only to more easily understand the present invention, and the content of the present invention are not limited by the following Examples.

Example 1. Identification of Effect of Inducing Direct Transdifferentiation into Neurons Using Metal Nanoparticles Magnetized by Electromagnetic Field The present invention is a technology of inducing direct transdifferentiation reprogramming of adult cells into neurons using electromagnetic-induced metal nanoparticles, and as an example, as illustrated in FIG. 1, fibroblasts pre-treated with a transcription factor were directly transdifferentiated into neurons by using a plate coated with gold nanoparticles, in which electromagnetism was induced by an electromagnetic field. More specifically, the present Example is intended to verify a change in activity of direct transdifferentiation into neurons according to the intensity and wavelength of an external electromagnetic field.

1-1. Change in Direct Transdifferentiation Efficiency According to Intensity of Electromagnetic Field In order to evaluate the activity of direct transdifferentiation of fibroblasts according to the change in intensity of the electromagnetic field, after an electromagnetic field at various intensities (10 G, 20 G, and 30 G) was applied to a plate coated with the gold nanoparticles, changes in tyrosine hydroxylase (TH) and Class III β-tubulin (Tuj1) which are neuronal marker genes were identified through immunostaining and fluorescence microscopy. Further, the expression degrees of Tuj1, microtubule associated protein 2 (MAP2), glutamic acid decarboxylase 67 (Gad67), and Synnapsin were quantitatively compared through real time PCR (RT-PCR). Meanwhile, a group to which the electromagnetic field was not applied was used as a control.

Figure 2A:
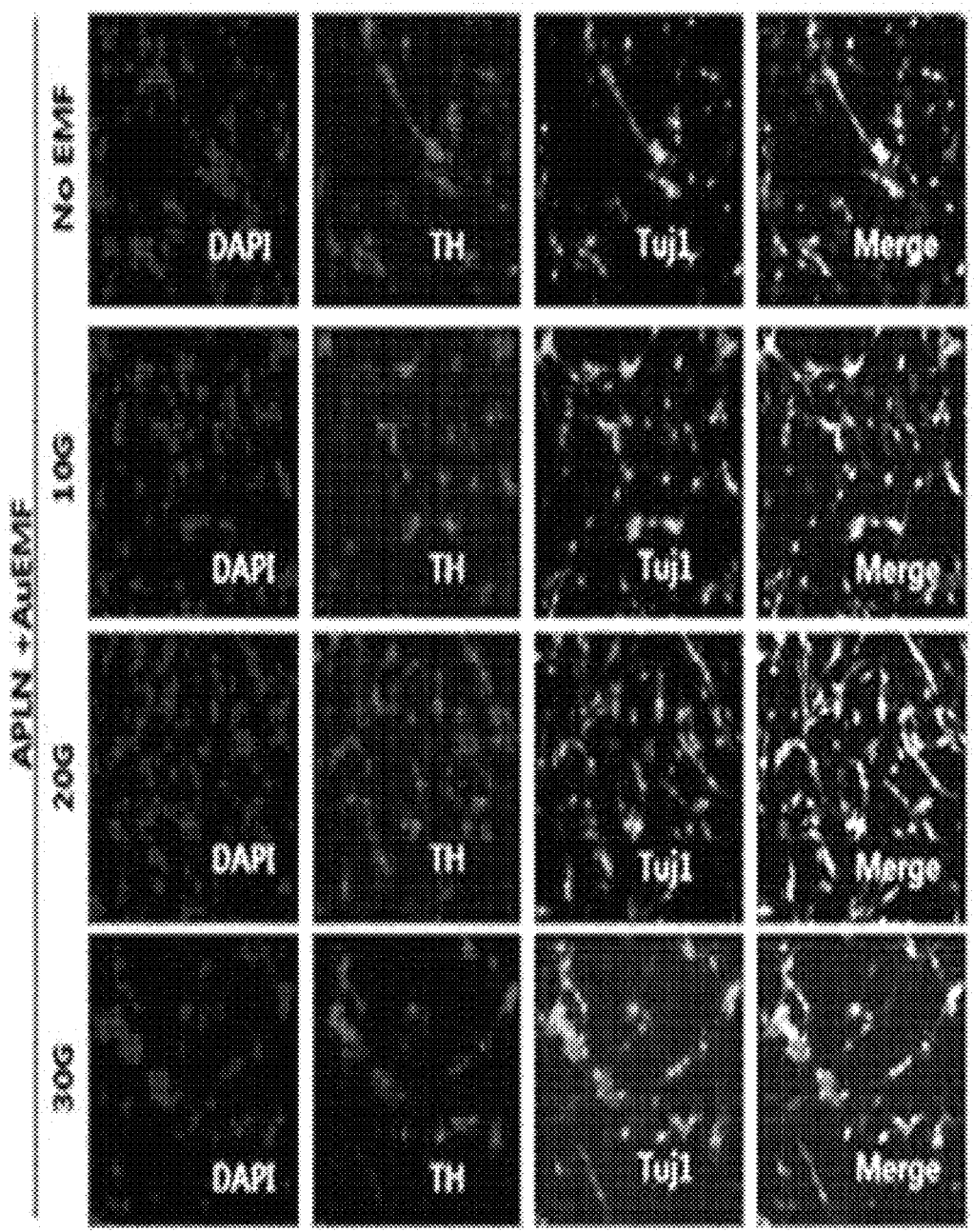
FIG. 2a is a result verifying a change in expression of TH and Tuj1 which are neuronal marker genes according to various intensities (10 G, 20 G, and 30 G) of an electromagnetic field through immunostaining and fluorescence microscopy.
Figure 2B:
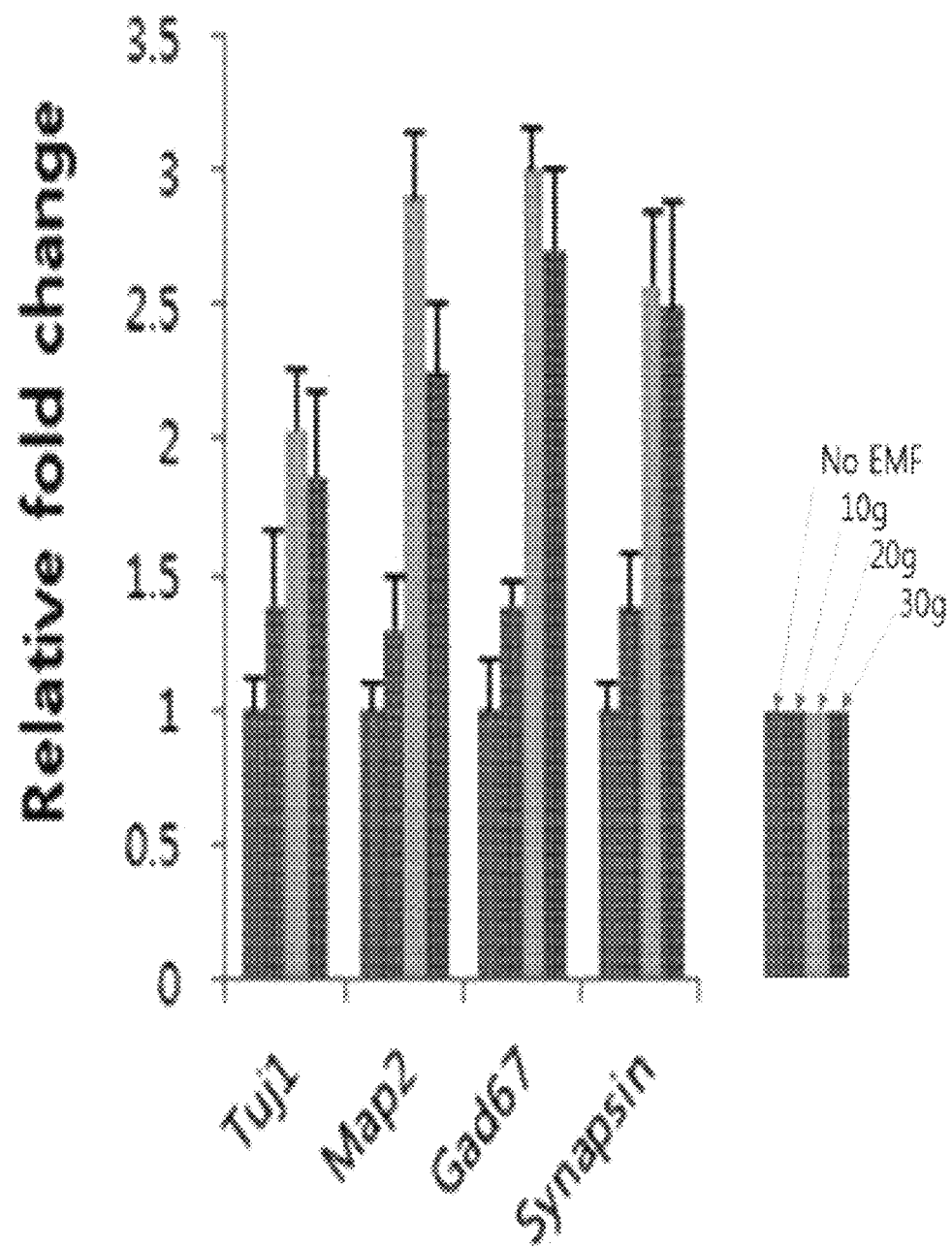
FIG. 2b is a result verifying the expression degree of Tuj1, MAP1, Gad67, and Synnapsin which are neuronal marker genes according to various intensities (10 G, 20 G, and 30 G) of an electromagnetic field through RT-PCR.

As a result, as illustrated in FIG. 2, it could be verified that in groups to which the electromagnetic field was applied in comparison with the control, TH and Tuj1, which are neuronal marker genes, were significantly increased, and among the groups, a group to which an electromagnetic field at 20 G was applied exhibited the best effect (see FIG. 2a). In addition, likewise as in the result, it could be verified that in the groups to which the electromagnetic field was applied, the expression amounts of Tuj1, MAP2, Gad67, and Synnapsin were all increased, and as compared to the expression amounts of the group to which the electromagnetic field at 10 G or 30 G was applied, the expression amounts of the group to which the electromagnetic field at 20 G was applied were remarkably increased (see FIG. 2b).

1-2. Change in Direct Transdifferentiation Efficiency According to Wavelength of Electromagnetic Field In order to evaluate the activity of direct transdifferentiation of fibroblasts according to the change in wavelength of the electromagnetic field, after an electromagnetic field at various intensities (10 G, 20 G, 30 G, 50 G, 100 G) and wavelengths (50 Hz, 150 Hz, and 250 Hz) was applied to a plate coated with the gold nanoparticles, the changes in the number of TH+ neurons per field were measured and compared.

As a result, as illustrated in FIG. 3, likewise as in Example 1-1, a plural number of TH+ neurons were measured from the group to which the electromagnetic field was applied as compared to the group to which the electromagnetic field was not applied. In particular, the number of cells was significantly decreased in the group to which the electromagnetic field at 30 G or more was applied, and the largest number of TH+ neurons was observed in the group to which the electromagnetic field at 20 G was applied. Further, among the groups to which the electromagnetic field at 20 G was applied, a plural number of TH+ neurons could be observed in the group to which the electromagnetic field at a frequency of 150 Hz or 250 Hz was applied.

Example 2. Identification of Effects of Efficiently Inducing Direct Transdifferentiation into Neurons Using Various Metal Nanoparticles In Example 1, direct transdifferentiation into neurons was induced using gold nanoparticles among metal nanoparticles and an electromagnetic field, whereas the present Example intended to verify whether the direct transdifferentiation efficiency into neurons could be enhanced even when various metal nanoparticles are used. Specifically, among metal nanoparticles, silver nanoparticles and magnetic nanoparticles were used, and the changes in aromatic amino acid decarboxylase (AADC) which is a neuronal marker gene by electromagnetic-induced silver or magnetic nanoparticles were quantitatively compared through RT-PCR.

Figure 4A:
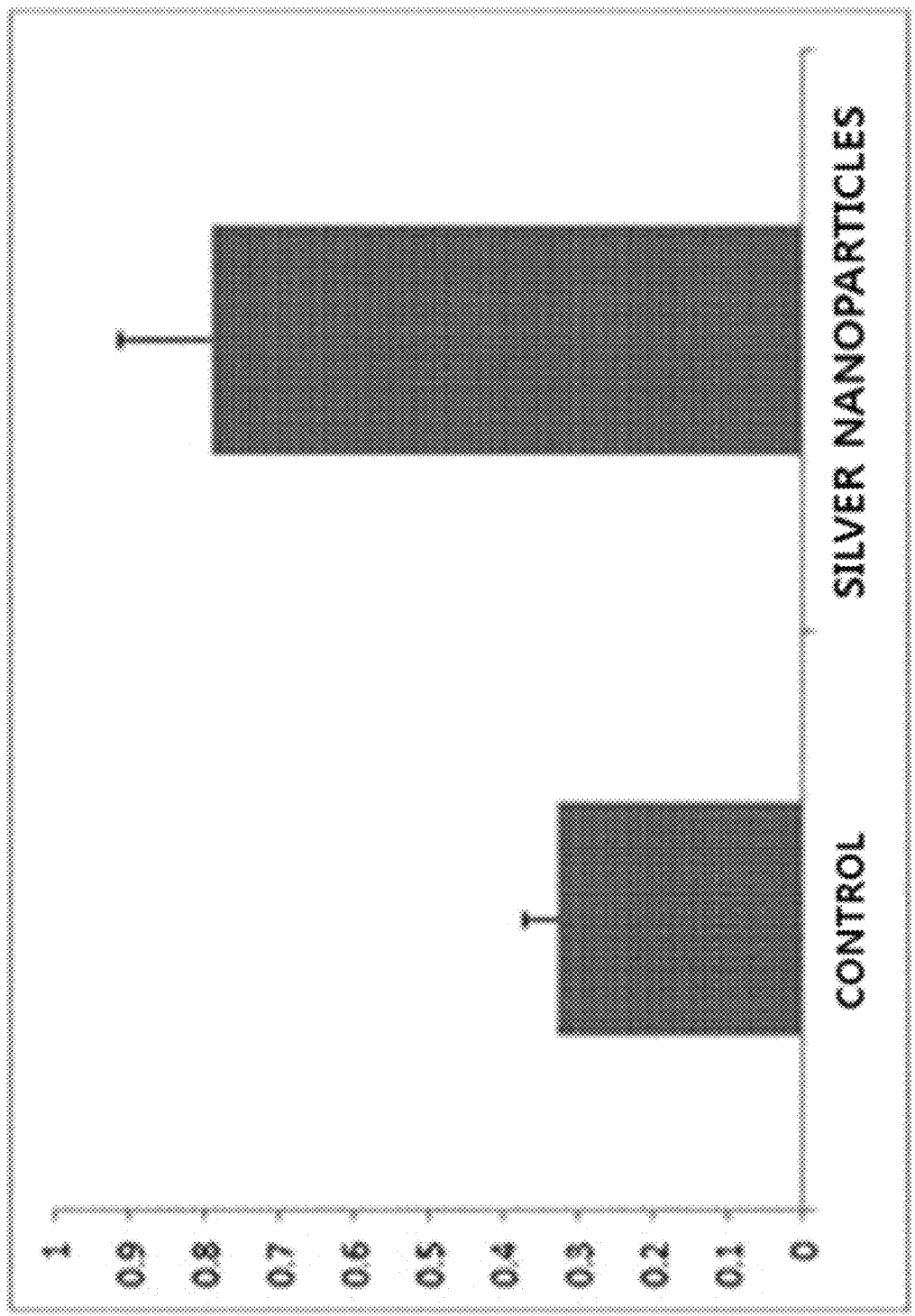
FIG. 4a is a result verifying a change of AADC which is a neuronal marker gene through RT-PCR when electromagnetic-induced silver nanoparticles are used.

As a result, as illustrated in FIG. 4, it was verified that in all the groups in which silver or magnetic nanoparticles were used, AADC was significantly increased as compared to the control which was not electromagnetically induced, and it could be verified that the direct transdifferentiation efficiency into neurons could be enhanced even when silver nanoparticles (see FIG. 4a) or magnetic nanoparticles (see FIG. 4b) were used.

Figure 5:
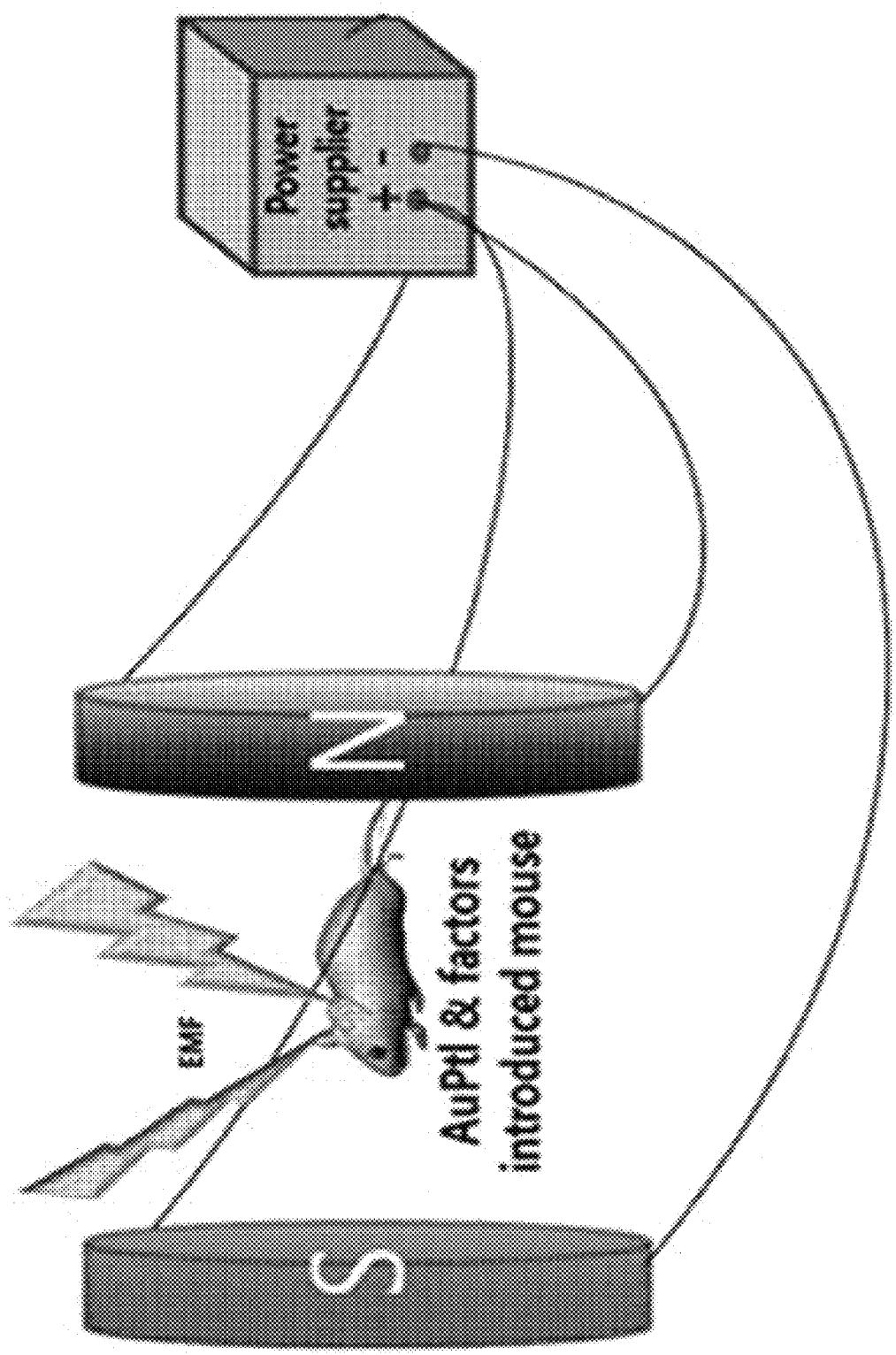
FIG. 5 is a view schematically illustrating the method for direct transdifferentiation reprogramming into neurons of the present invention in an in vivo animal model.

Example 3. Identification of Effects of Inducing Direct Transdifferentiation into Neurons in Animal Model The present Example intended to verify effects of inducing direct transdifferentiation into neurons according to the present invention in vivo by using an animal model. For this purpose, as illustrated in FIG. 5, Ascl1, Nurr1, Pitx3, and Lmx1, which are transcription factors, and gold nanoparticles were injected into the brain of a mouse and an electromagnetic field was applied thereto, and in this case, the changes in TH and Tuj1 which are neuronal marker genes were identified through immunostaining and fluorescence microscopy. As a control, a group (Auptl), to which the transcription factor and metal nanoparticles were administered and the electromagnetic field was not applied, was used.

Figure 6:
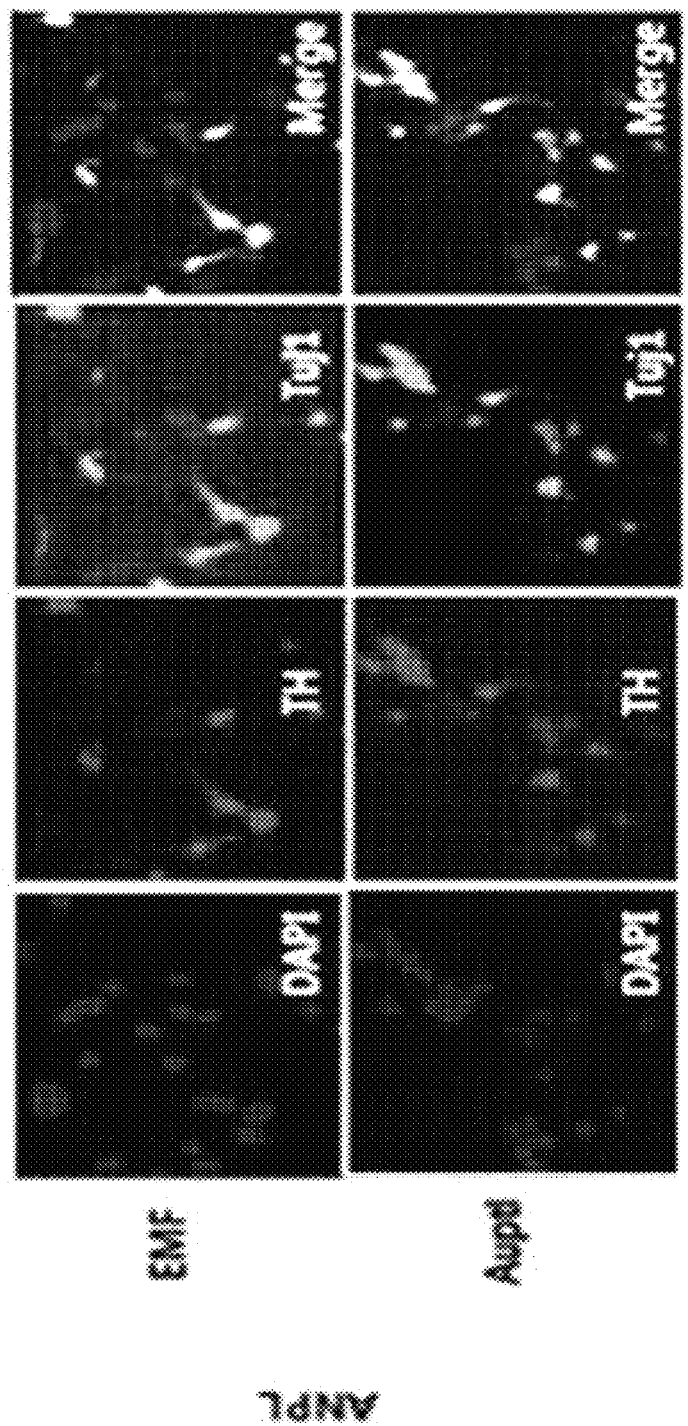
FIG. 6 is a result verifying a change of TH and Tuj1 which are neuronal marker genes through immunostaining and fluorescence microscopy when a transcription factor and gold nanoparticles are injected into the brain of a mouse and an electromagnetic field is applied to the animal, in an animal model.

As a result, as illustrated in FIG. 6, in the group (EMF) to which the electromagnetic field was applied as compared to the control, TH and Tuj1 were significantly increased, meaning that the direct transdifferentiation into neurons can be promoted even in vivo through the method of the present invention.

Example 4. Identification of Effects of Treating Cerebral Nerve Disease According to Induction of Direct Transdifferentiation The present Example intended to identify the effects of treating cerebral diseases of the present invention using an animal model, based on the result of Example 3. More specifically, effects of alleviating cerebral nerve symptoms were compared in a cerebral nerve injury according to the treatment with 6-hydroxydopamine (6OHDA) or 1-methyl-4-phenyl-1,2,3,6-tetrahydropyridine (MPTP) and recuperation therefrom and a stroke animal model.

4-1. Protective Effect Against 6-Hydroxydopamine (6OHDA)

Dopaminergic neurons were subjected to necrosis by injecting 6-hydroxydopamine (6OHDA) which is a Parkinson's disease-inducing drug into the brain of a mouse. Thereafter, when the brain of the mouse was treated with a nanomaterial having conductivity, such as gold nanoparticles or silver nanoparticles, and an electromagnetic field was applied thereto, the protective effect of neurons was identified through a change in the number of rotations of the mouse. As a control, a group, which was not treated with metal nanoparticles and the electromagnetic field, was used.

Figure 7A:
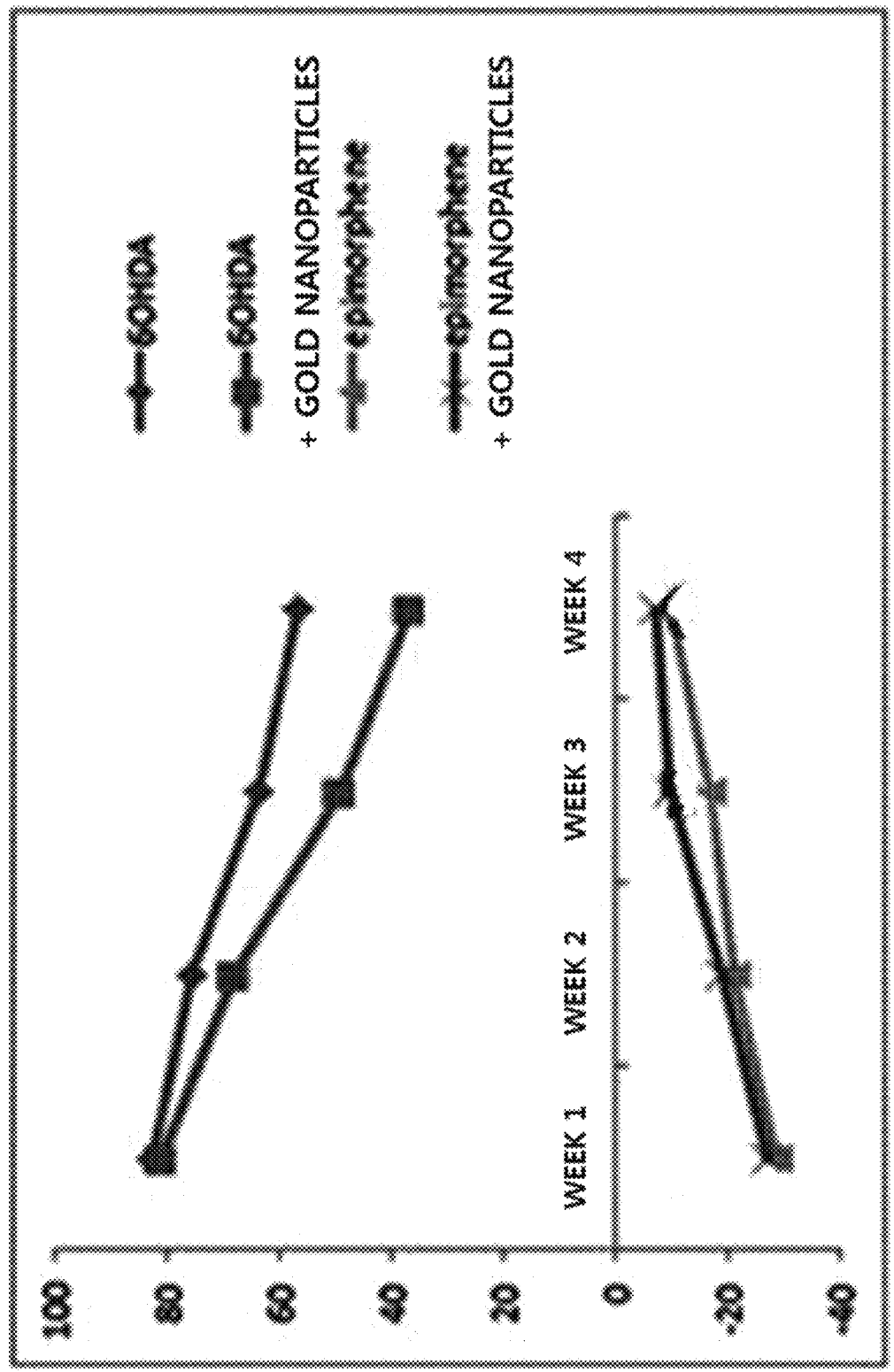
FIG. 7a is a result verifying a restoration effect of cerebral nerves of a mouse through the change in the number of rotations when a transcription factor and gold nanoparticles are injected into the brain of the mouse and an external electromagnetic field is applied thereto in an animal model into which a Parkinson's disease-inducing drug 6OHDA is introduced.
Figure 7B:
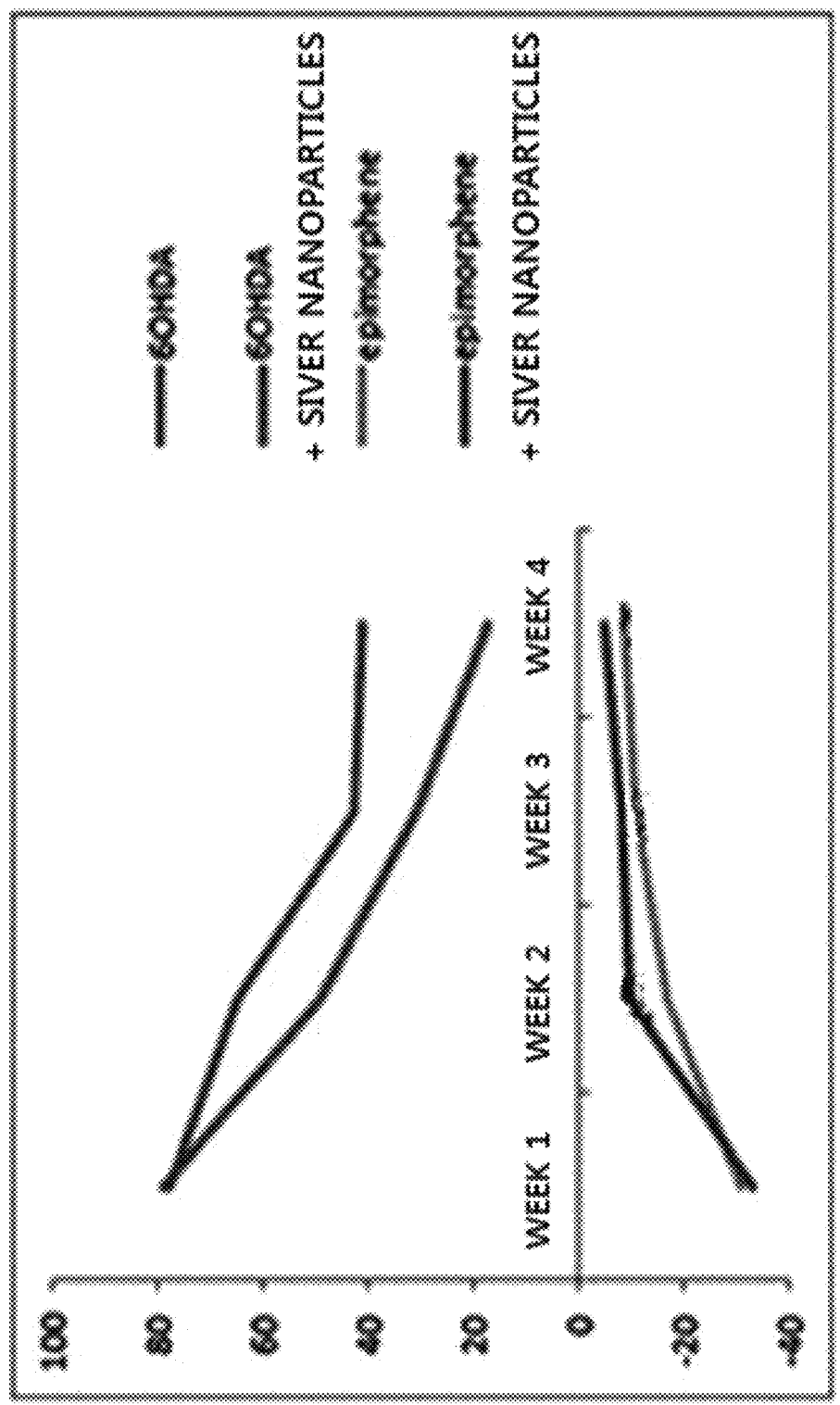
FIG. 7b is a result verifying a restoration effect of cerebral nerves of a mouse through the change in the number of rotations when a transcription factor and silver nanoparticles are injected into the brain of the mouse and an external electromagnetic field is applied thereto in an animal model into which a Parkinson's disease-inducing drug 6OHDA is introduced.

As a result, as illustrated in FIG. 7, the number of rotations of the mouse was increased by injecting 6OHDA, whereas when a transcription factor and gold nanoparticles (see FIG. 7a) or silver nanoparticles (see FIG. 7b) were injected and an electromagnetic field was applied thereto, direct transdifferentiation into neurons was induced, and as a result, the number of rotations of the mouse was remarkably decreased by an external drug. That is, it could be verified that metal nanoparticles such as gold nanoparticles or silver nanoparticles can considerably alleviate the rotational behavior of the mouse due to the injury of dopaminergic neurons by inducing the treatment of Parkinson's disease.

4-2. Protective Effect against 1-methyl-4-phenyl-1,2,3,6-tetrahydropyridine (MPTP)

First, neurons were artificially destroyed by treatment with 1-methyl-4-phenyl-1,2,3,6-tetrahydropyridine (MPTP) which is a substance which destroys neurons. Thereafter, when the brain of a mouse was treated with a transcription factor and gold nanoparticles and an electromagnetic field was applied thereto, the protective effects of neurons were identified through an immunostaining method. Further, a neural disease mouse animal model induced by MPTP was prepared, and the change in behavior of the mouse according to the treatment of the transcription factor, gold nanoparticles and electromagnetic field was observed through a cylinder test, a pole test, or the locomotor test. As a control, a group (Cont, No AuEMF), which was not treated with the metal nanoparticles and the electromagnetic field, was used.

Figure 8A:
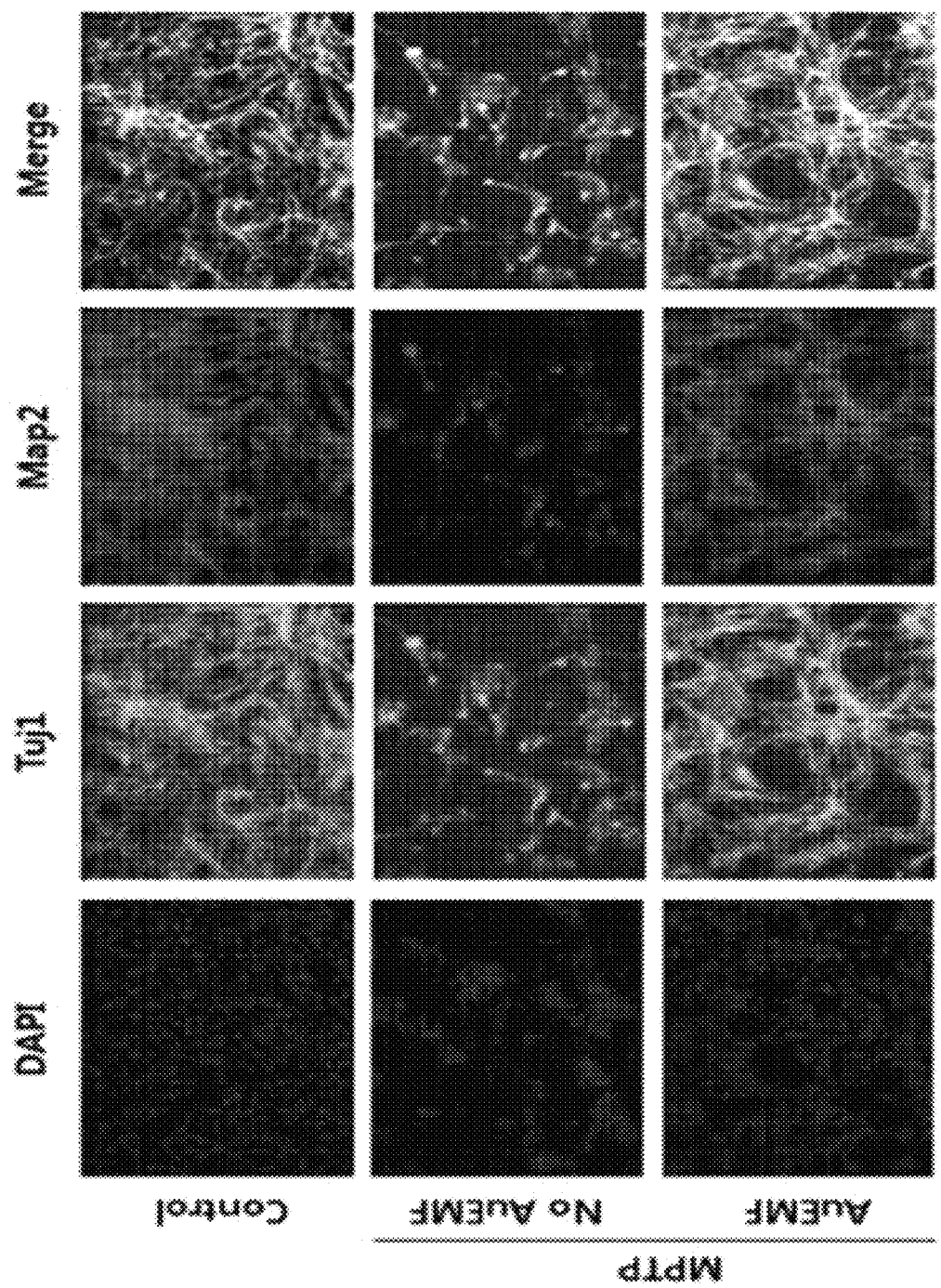
FIG. 8a is a result verifying the changes in Tuj1 and Map2, which are neuronal marker genes, through fluorescence microscopy after the genes are stained using an immunostaining method when the brain of a mouse is treated with a transcription factor and gold nanoparticles and an electromagnetic field is applied thereto in an animal model which is treated with 1-methyl-4-phenyl-1,2,3,6-tetrahydropyridine (MPTP) which is a substance which destroys neurons.
Figure 8B:
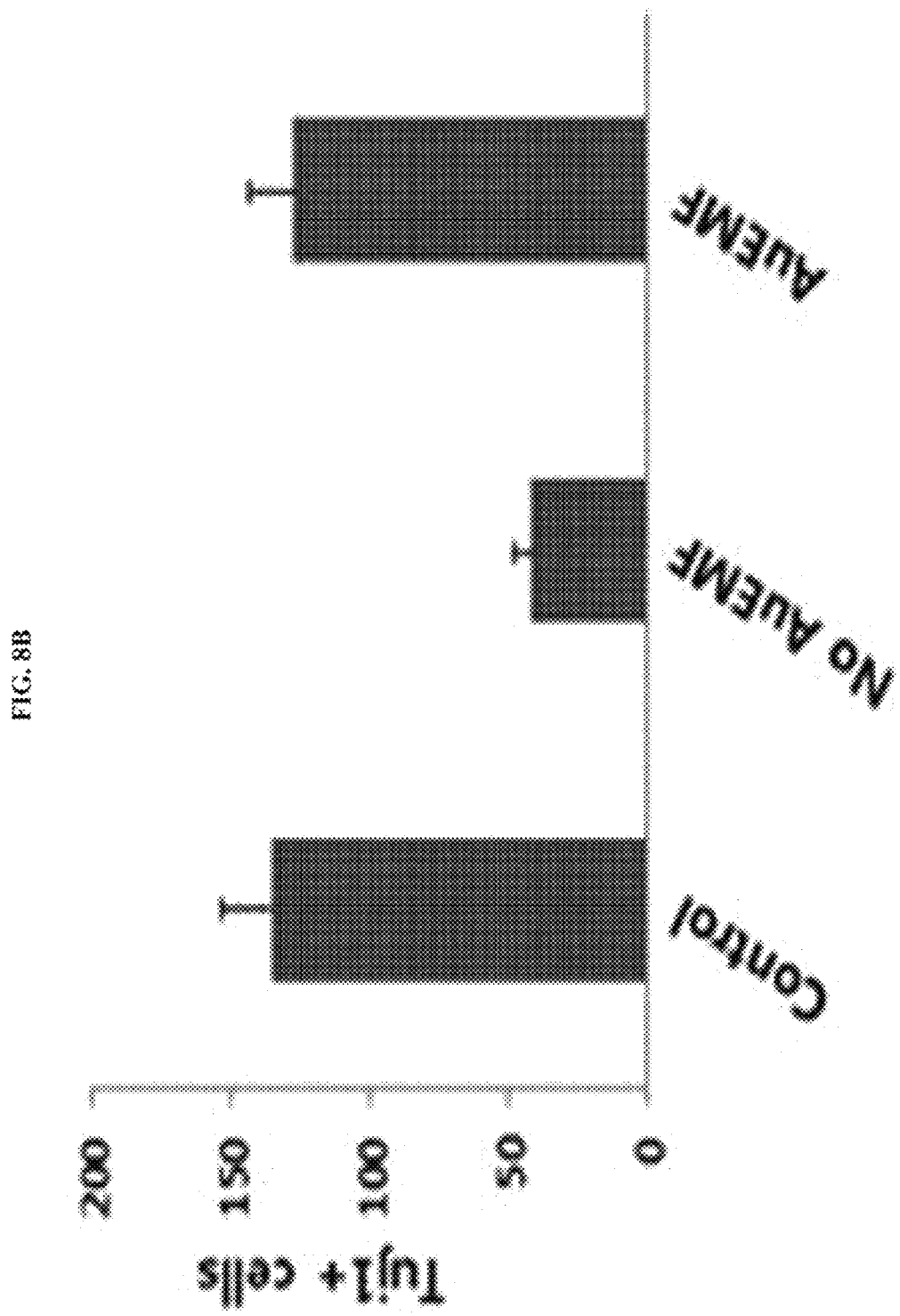
FIG. 8b is a result quantifying and verifying a change in Tuj1 which is a neuronal marker gene when the brain of a mouse is treated with a transcription factor and gold nanoparticles and an electromagnetic field is applied thereto in an animal model which is treated with MPTP which is a substance which destroys neurons.
Figure 8C:
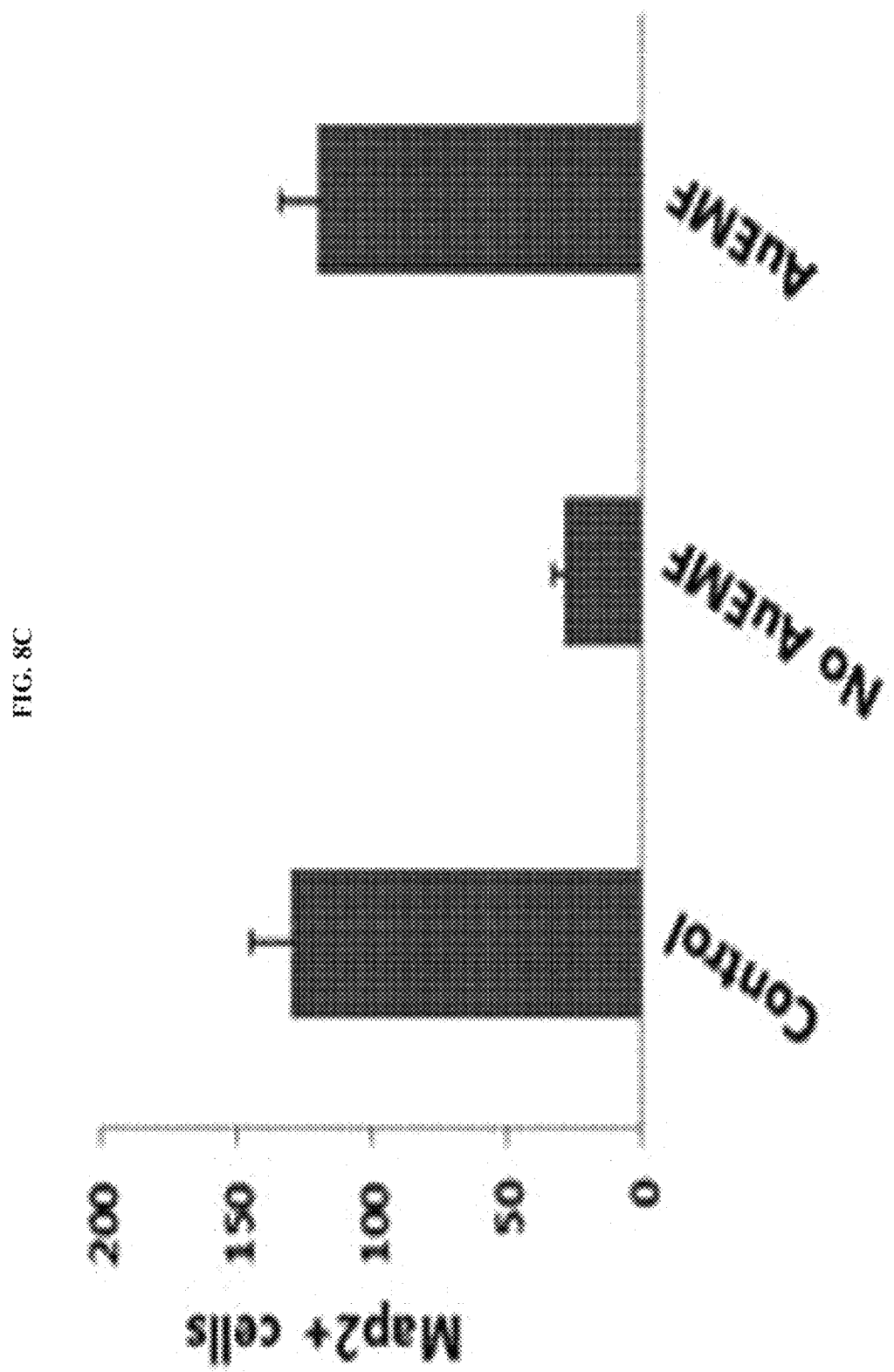
FIG. 8c is a result quantifying and verifying a change in Map2 which is a neuronal marker gene when the brain of a mouse is treated with a transcription factor and gold nanoparticles and an electromagnetic field is applied thereto in an animal model which is treated with MPTP which is a substance which destroys neurons.

As a result, as illustrated in FIG. 8, Tuj1 and Map2, which are neuronal marker genes, were significantly decreased by the treatment with MPTP, whereas when a transcription factor and gold nanoparticles were injected into the mouse and the electromagnetic field was applied thereto, Tuj1 and Map2, which are neuronal marker genes, were slightly decreased, and a significant protective effect of neurons could be identified.

Figure 9:
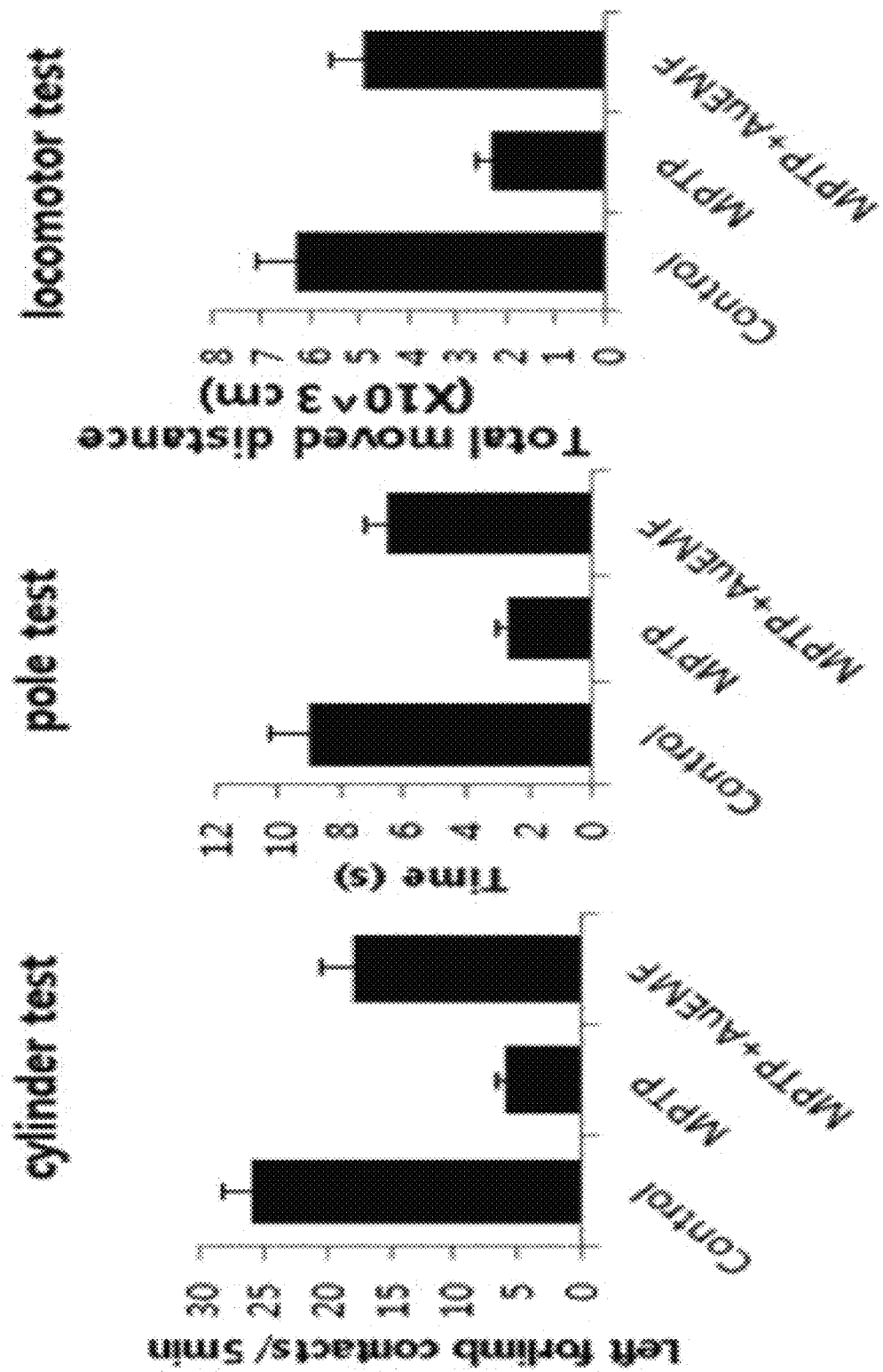
FIG. 9 is a result verifying a restoration effect of cerebral nerves of a mouse through bending, limb, and tape-self detachment tests when a transcription factor and gold nanoparticles are injected into the brain of the mouse and an external magnetic field is applied thereto in a cerebral nerve disease mouse animal model induced by MPTP.

Furthermore, as illustrated in FIG. 9, as a result of the cylinder test, the pole test, or the locomotor test, it could be verified that when gold nanoparticles were injected and the electromagnetic field was applied thereto, direct transdifferentiation into neurons was induced, and as a result, abnormal behavior of the mouse caused by a stroke were considerably improved.

4-3. Therapeutic Effect in Stroke Animal Model

When a stroke model was prepared, and then the brain of the stroke mouse was treated with the transcription factor and the metal nanoparticles, and the electromagnetic field was applied thereto, the change in behavior of the mouse exhibited from a stroke was observed through bending, limb, and tape-self detachment tests. As a control, a group (MPTP), which was not treated with the metal nanoparticles and the electromagnetic field, was used.

Figure 10:
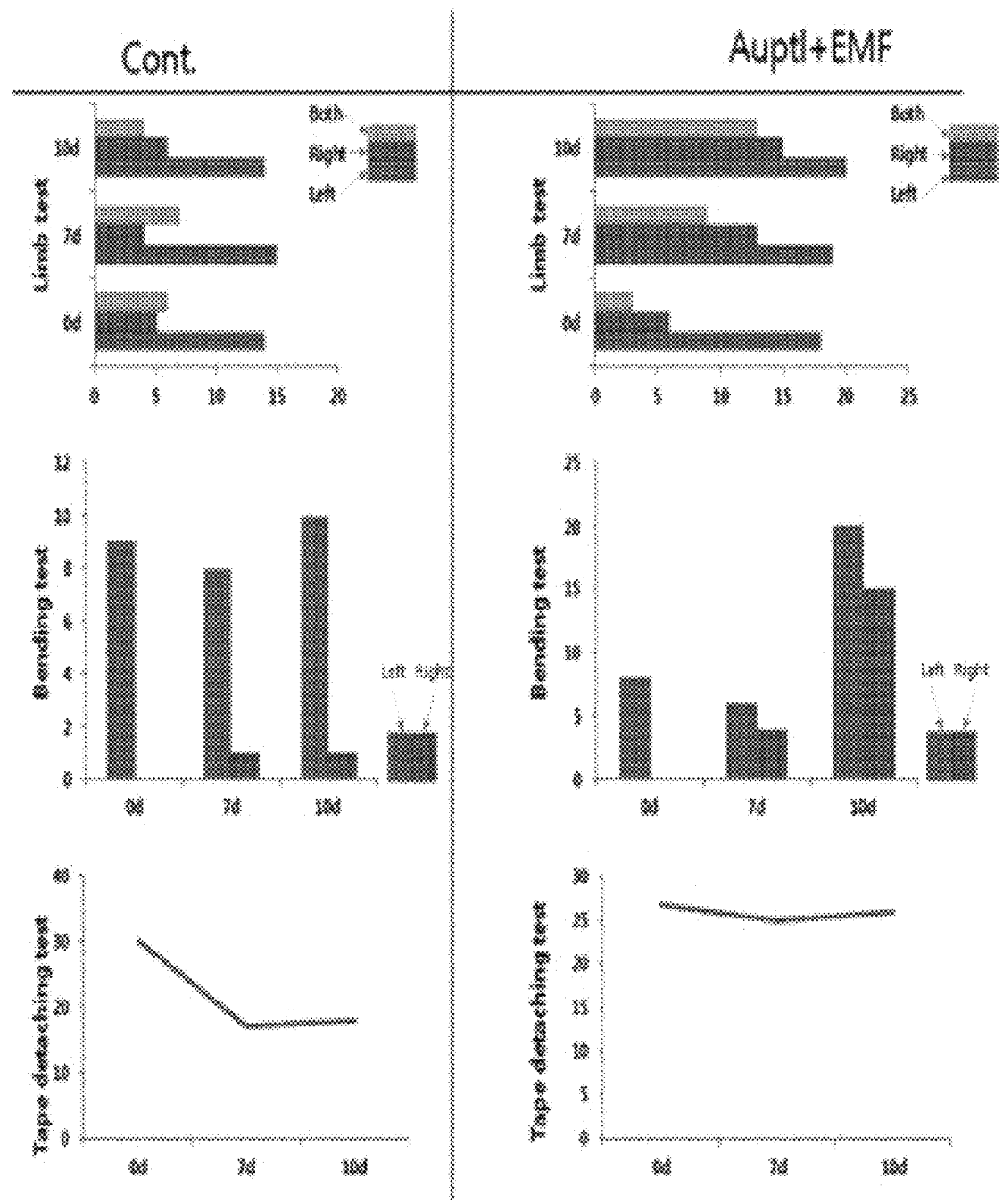
FIG. 10 is a result verifying a restoration effect of cerebral nerves of a mouse through bending, limb, and tape-self detachment tests when a transcription factor and gold nanoparticles are injected into the brain of the mouse and an external magnetic field is applied thereto in a stroke animal model.

As a result, as illustrated in FIG. 10, abnormal behavior of the mouse caused by the stroke was increased, whereas when the transcription factor and the metal nanoparticles were injected into the mouse and the electromagnetic field was applied thereto, it could be verified that direct transdifferentiation into neurons was induced, and as a result, abnormal behavior of the mouse was decreased.

Example 5. Identification of Effects of Inducing Natural Differentiation into Neurons Using Metal Nanoparticles Magnetized by Electromagnetic Field In Examples 1 to 4, direct transdifferentiation reprogramming from fibroblasts, which are adult cells, to neurons was induced using metal nanoparticles magnetized by an electromagnetic field, whereas the present Example intended to verify whether a natural differentiation inducing efficiency from embryonic stem cells to neurons could also be enhanced using the present invention. More specifically, when embryonic stem cells were treated with gold nanoparticles, and then the electromagnetic field was applied thereto, natural differentiation into neurons was identified through an immunostaining method, and changes in expression amounts of Map2, Tuj1, Vmat2, Nestin, TH, DAT, and Pitx3, which are neuronal marker genes were identified through RT-PCR. As a control, a group (Control), which was not treated with the metal nanoparticles and the electromagnetic field, was used.

Figure 11A:
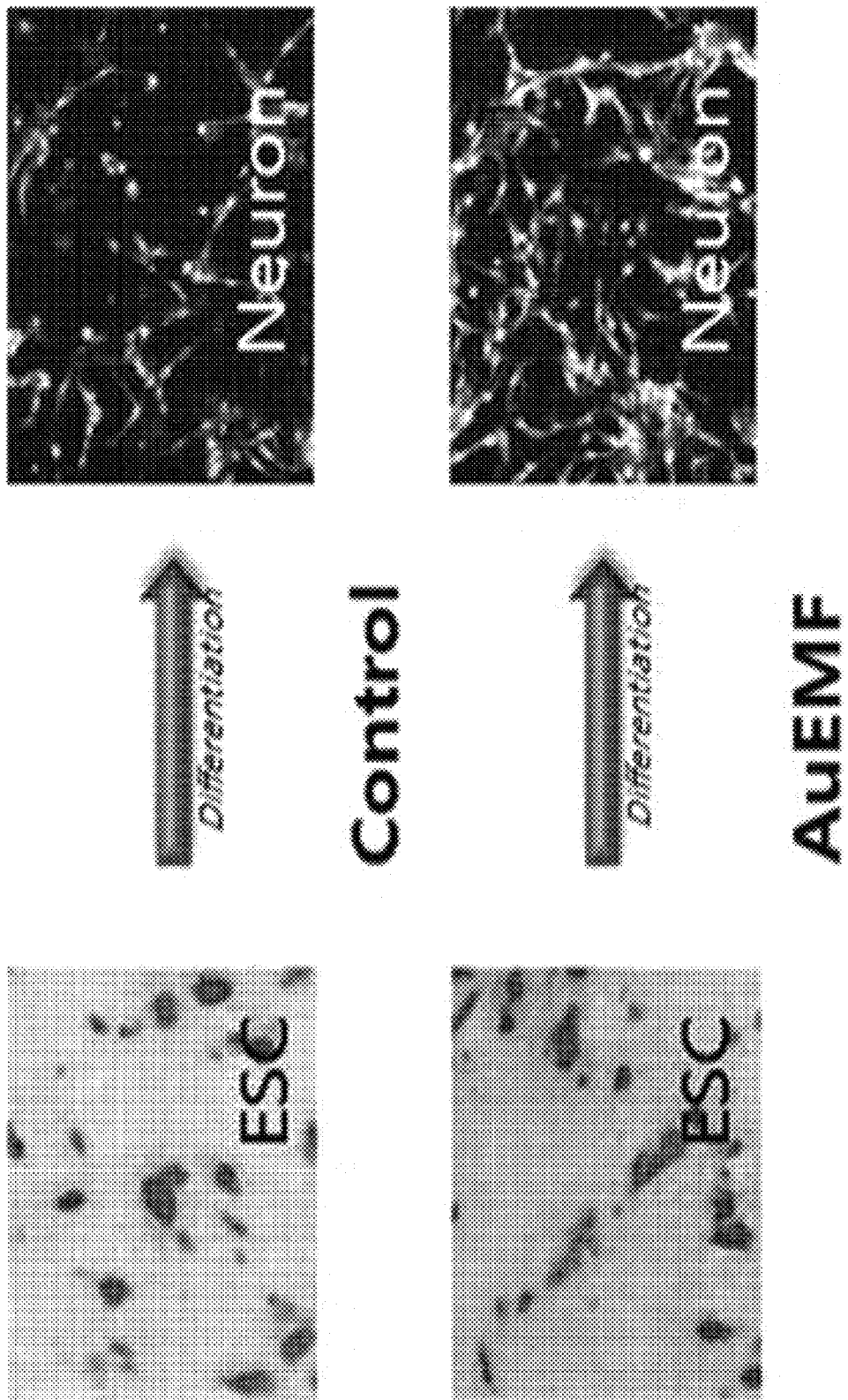
FIG. 11a is a result verifying a change in the number of differentiated neurons through fluorescence microscopy after the cells are stained using an immunostaining method when natural differentiation from embryonic stem cells into neurons is induced using electromagnetic-induced gold nanoparticles.
Figure 11B:
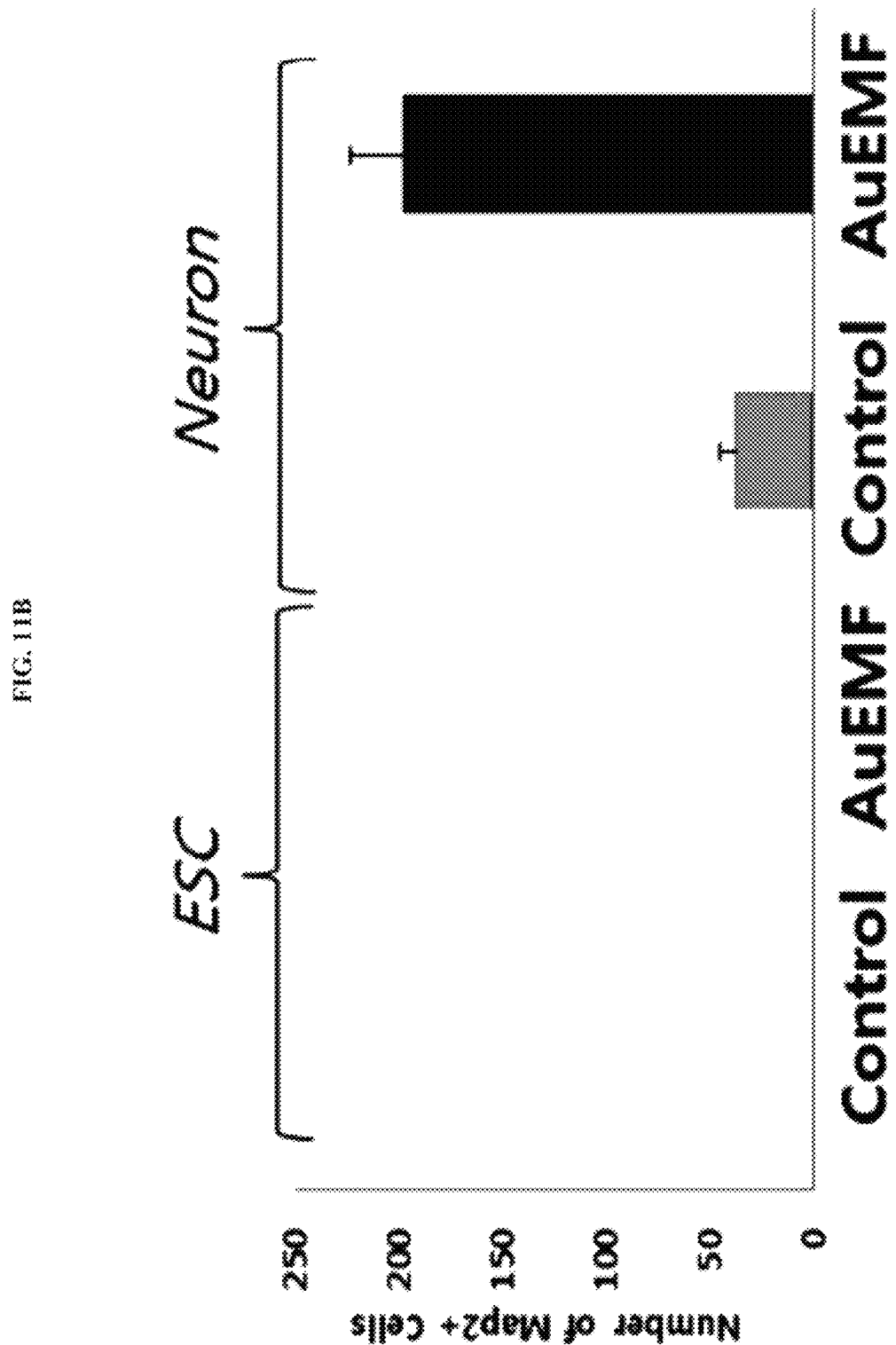
FIG. 11b is a result quantifying and verifying a change in the number of Map2+ neurons when natural differentiation from embryonic stem cells into neurons is induced using electromagnetic-induced gold nanoparticles.
Figure 11C:
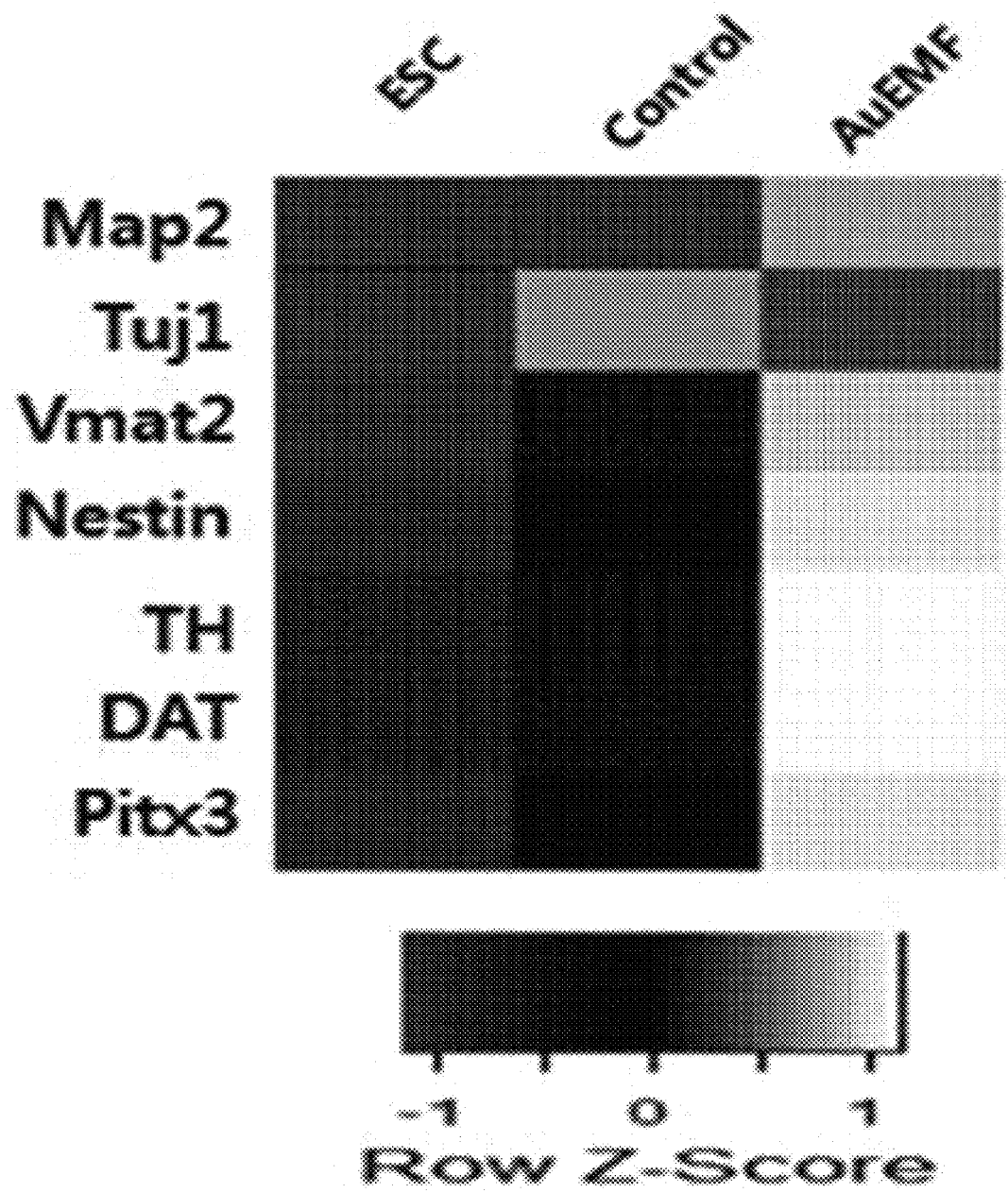
FIG. 11c is a result verifying the changes in expression amounts of Map2, Tuj1, Vmat2, Nestin, TH, DAT, and Pitx3, which are neuronal marker genes, in the form of a heatmap by analyzing the changes in expression amounts through RT-PCR when natural differentiation from embryonic stem cells into neurons is induced using electromagnetic-induced gold nanoparticles.

As a result, as illustrated in FIG. 11, when the electromagnetic field was applied after the treatment with gold nanoparticles, a natural differentiation efficiency into neurons was remarkably increased as compared to the control (see FIG. 11a), and likewise as in the above result, it could be verified that the expression amounts of Map2, Tuj1, Vmat2, Nestin, TH, DAT, and Pitx3, which are neuronal marker genes were also remarkably increased, through RT-PCR. This means that through the method of the present invention, direct transdifferentiation reprogramming into neurons and a natural differentiation efficiency into neurons can be improved.

Example 6. Identification of Effects of Treating Cerebral Nerve Disease According to Induction of Natural Differentiation The present Example intended to identify the effects of treating cerebral diseases of the present invention using an animal model, based on the result of Example 5. More specifically, neurons naturally differentiated from embryonic stem cells were transplanted into a neural disease mouse animal model induced by MPTP through the method of the present invention, and the change in behavior of the mouse according to the transplantation was observed through a cylinder test and a locomotor test. As a control, a group (Control), in which neurons were not transplanted, was used.

Figure 12:
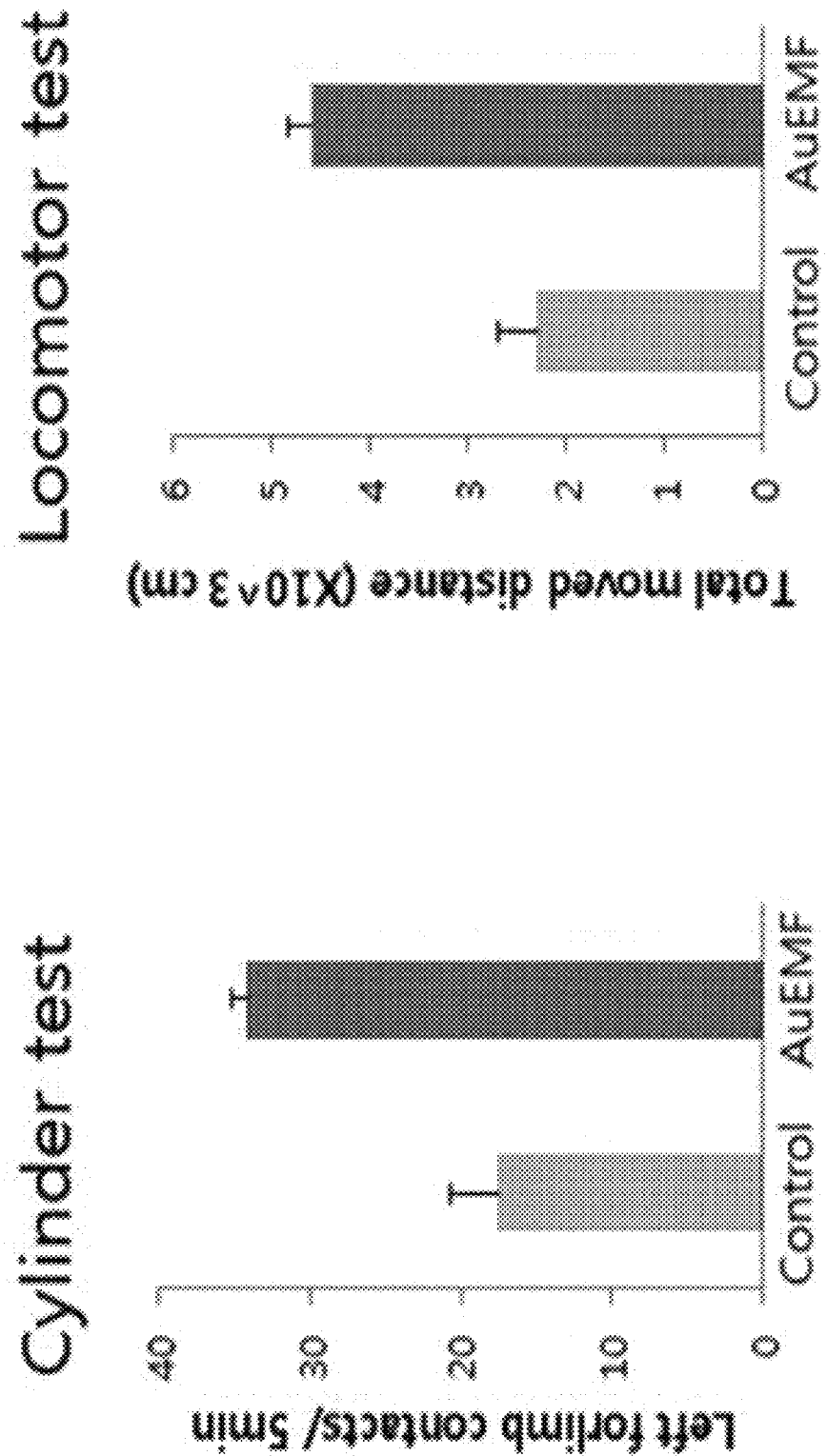
FIG. 12 is a result verifying a restoration effect of cerebral nerves of a mouse through a cylinder test and a locomotor test when neurons naturally differentiated from embryonic stem cells are transplanted into a cerebral nerve disease mouse animal model induced by MPTP.

As a result, as illustrated in FIG. 12, it could be verified that when neurons naturally differentiated from embryonic stem cells were transplanted through the method of the present invention, abnormal behavior of the MPTP mouse was considerably improved as compared to the control. From the result, it could be verified that neurons naturally differentiated through the method of the present invention using electromagnetic-induced gold nanoparticles could be usefully used for the treatment of cerebral nerve diseases.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are only illustrative in all aspects and are not restrictive.

INDUSTRIAL APPLICABILITY

A method for direct transdifferentiation reprogramming into neurons according to the present invention induces reprogramming into neurons using electromagnetic-induced metal nanoparticles, and in the present invention, it was specifically verified that the direct transdifferentiation reprogramming efficiency into neurons in vivo and in vitro can be remarkably improved through the above method and when this technology is applied to the brain in vivo, symptoms of cerebral nerve diseases, such as Alzheimer's disease, Parkinson's disease, cerebral infarctions, and cerebral hemorrhages, can be effectively alleviated through neuranagenesis. Therefore, the method is expected to be usefully used as a technology for the treatment of cerebral nerve diseases.

The invention claimed is:

1. A method for direct transdifferentiation of adult cells into neurons, the method comprising applying an electromagnetic field to metal nanoparticles brought into non-invasive contact with adult cells into which a transcription factor is introduced,
   wherein the transcription factor is a combination of Ascl1, Nurr1, Pitx3, and Lmx1;
   wherein the adult cells are fibroblasts or astrocytes; and
   wherein the metal nanoparticles are selected from the group consisting of gold nanoparticles and silver nanoparticles.

2. The method of claim 1, wherein the adult cells are fibroblasts.

3. The method of claim 1, wherein the electromagnetic field is applied at an intensity of 5 Gauss to 100 Gauss.

4. The method of claim 1, wherein the electromagnetic field is applied at a frequency of 10 Hz to 500 Hz.

5. The method of claim 1, wherein the direct transdifferentiation is one selected from a group consisting of in vitro direct transdifferentiation reprogramming and in vivo direct transdifferentiation reprogramming.

* * * * *